United States Patent
Kelley et al.

(10) Patent No.: US 7,585,550 B2
(45) Date of Patent: Sep. 8, 2009

(54) PROCESS FOR MODIFYING POLYMERIC SURFACES USING DEEP UV IRRADIATION

(75) Inventors: Michael J Kelley, Newport News, VA (US); Zhengmao Zhu, Williamsburg, VA (US)

(73) Assignee: College of William and Mary, Williamsburg, VA (US)

( * ) Notice: Subject to any disclaimer, the term of this patent is extended or adjusted under 35 U.S.C. 154(b) by 838 days.

(21) Appl. No.: 11/047,939

(22) Filed: Feb. 1, 2005

(65) Prior Publication Data

US 2005/0170193 A1    Aug. 4, 2005

Related U.S. Application Data

(60) Provisional application No. 60/541,416, filed on Feb. 2, 2004.

(51) Int. Cl.
*C08J 7/18* (2006.01)
(52) U.S. Cl. .................. 427/553; 427/508; 427/509; 427/532
(58) Field of Classification Search .................. 427/554, 427/508–520, 553–559, 532
See application file for complete search history.

(56) References Cited

U.S. PATENT DOCUMENTS

| 4,026,809 | A | * | 5/1977 | Lachowicz et al. | .......... 508/470 |
| 4,134,514 | A | * | 1/1979 | Schumacher et al. | ........ 220/694 |
| 5,428,078 | A | * | 6/1995 | Cohen et al. | ................... 522/2 |
| 6,022,553 | A | * | 2/2000 | Anders et al. | ............... 424/411 |
| 6,537,411 | B1 | | 3/2003 | Kang | |
| 6,861,006 | B2 | | 3/2005 | Ferain | |

OTHER PUBLICATIONS

Lazare et al. J.Am. Chem. Soc. "Controlled Modification of Organic Polymer Surfaces by Continuous Wave Far-Ultraviolet (185 nm) and Pulsed-Laser (193 nm) Radiation: XPS Studies" 1984, vol. 106, pp. 4288-4290.*

Hozumi et al. "Molecular-Scale Growth of Silicon Oxide on Polymer Substrate Through Vacuum Ultraviolet Light-Assisted Photooxidation of Organosilane Precursor" Thin Solid Films 437 (2003) 89-94.*

Dunn, D.S.; and Ouderdirk, A.J. "Chemical and Physical Properties of Laser Modified Polymers", Macromolecules, 1990, p. 770-774, vol. 23.

Chtaib, M.; Roberfroid, E.M.; Novis, Y; Pireaux, J.J., and Caudano, R. "Polymer surface reactivity . . . ", J. Vac. Sci. Technol., 1989, p. 3233, vol. A 7.

Lazare, S.; and Srinivasan, R. "Surface Properties of Poly(ethylene terephtalate) Films . . . ", J. Phys. Chem., 1986, p. 2124-2131, vol. 90.

Praschak, D.; Bahners, T.; and Schollmeyer, E. "PET surface modifications by treatment . . . ", Appl. Phys. A, 1998, p. 69-75, vol. 66.

Ranby, B.; Yang, W.T.; and Tretinnikov, O. "Surface photografting of polymer fibers . . . ", Nuclear Instruments and Methods in Physics Research B, 1999, p. 301-305, vol. 151.

* cited by examiner

*Primary Examiner*—Michael Kornakov
*Assistant Examiner*—Robert S Walters, Jr.
(74) *Attorney, Agent, or Firm*—Jason P. McDevitt

(57) ABSTRACT

A process is described for modifying polymeric surfaces. The process is particularly useful for modification of polyesters, and can be used to impart surface functionality that confers antimicrobial, anti-soiling, or other desirable properties to the polymer. The process comprises the steps of exposing a polymeric substrate to deep UV irradiation, followed by reaction with a grafting agent. In preferred embodiments, a vapor-phase grafting agent undergoes covalent reactions with the UV-modified polymer surface to produce a polymer with improved properties.

5 Claims, 16 Drawing Sheets

PROCESS FOR MODIFYING POLYMERIC SURFACES USING DEEP UV IRRADIATION

CROSS-REFERENCE TO RELATED APPLICATIONS

This application is based upon and claims priority to U.S. Provisional Patent Application No. 60/541,416, filed Feb. 2, 2004.

STATEMENT REGARDING FEDERALLY SPONSORED RESEARCH OR DEVELOPMENT

Not Applicable

BACKGROUND OF THE INVENTION

Many commercial polymers exist in the marketplace today. These polymers have a variety of applications and are exposed to a variety of environments. The value of many of these commercial polymers can be increased by enhancing the surface or interface properties of the polymers in a cost-effective manner. Examples of these properties include but are not limited to: adhesion, permeability, anti-soiling, and antimicrobial properties. Polyesters (in particular, polyethylene terephthalate (PET)) are of particular interest because of their widespread use in textiles and packaging. The processing of these materials is highly cost-sensitive.

Some polymers contain reactive or potentially reactive carboxylic acid surface sites that are useful for a number of applications. Such applications include grafting, wetting, dyeing, and adsorption. However, common commercial polyesters (such as PET) have very few acid sites, making it difficult to modify the surface of the polyester via chemical reaction. In an effort to improve surface modification, methods have been developed to add carboxylic acid sites to the polymer surface. However, providing acid sites to these polymers by modifying their bulk chemistries (for example, by incorporating additives) increases cost and process complexity, and may adversely affect other physical or chemical properties of the polymers. Alternatively, providing carboxylic acid sites by coating a polymer film with a layer of a polymer having the desired functionality adds cost and weight, and may involve the use of environmentally unfriendly or expensive chemicals and processes.

A need exists for a process wherein the concentration of acid groups on the surface of polymers is increased without adversely affecting the bulk properties or the surface topography of the polymer. The present invention solves this problem by providing a process for surface modification that utilizes deep ultraviolet (UV) irradiation. There are few reported studies of the effect of deep UV (that is, wavelengths below 250 nm) on PET surface chemistries. No effect was found by X-ray photoelectron spectroscopy (XPS) for excimer laser irradiation in air at 248 nm of biaxially oriented PET film at 12 mJ/cm$^2$ (below the ablation threshold) (Dunn, Ouderkirk, *Macromolecules*, Vol. 23 (1990) p. 770). Upon irradiation at 193 nm in a nitrogen atmosphere, a loss of oxygen-containing species is evident by XPS even at 10 mJ/cm$^2$ (Chtaib, et al., *J. Vac. Sci. Technol.*, Vol. A 7 (1989) p. 3233). This study showed that C—O bonds were affected more than C=O bonds. Even though the fluence in both excimer laser studies was below the ablation threshold, thermal effects were not absent, since the polymer was amorphized in both cases. Irradiation with 185 nm Hg vapor light in vacuum led to reduced surface oxygen as seen by XPS, but increased uptake of derivatizing reagents for carboxyl functionality. In contrast, repeating the experiment with a filter that excluded 185 nm emission and passed only the 254 nm component resulted in little or no effect (Lazare, Srinivasan, *J. Phys. Chem.*, Vol. 90 (1986) p. 2124),consistent with the 248 nm observations. Irradiation in nitrogen at 222 nm (KrCl excimer lamp) resulted in a modest increase in surface oxygen species as seen by XPS, but only after 500 J/cm$^2$ (Praschak, et al., *Appl. Phys.*, Vol. A 66 (1998) p.69). At this fluence level, the question of a possible role for residual oxygen in the treatment cell atmosphere is hard to avoid.

Grafting implies attachment of a species to the polymer surface by covalent chemical bonds. Among the processes that can be used to obtain a desired surface chemistry, grafting is particularly appealing in that added species are strongly attached, the amount of added material is minimized, and the prospects for adversely impacting the original properties of the substrate are minimized. Since grafting is a chemical reaction, the substrate to be coated and the grafting reagent must provide reactive sites, or reactive sites must be created during the process. Wet chemical methods are well-known to those skilled in the art, but require contacting the substrate surface with fluids containing the required chemical species. Application, removal, and disposal of successive fluids contributes complexity and thus cost to a grafting process. Relief from these burdens may be sought by using an appropriate wavelength of light to supply the energy needed to drive the chemistry. As described in a recent review [Rånby, Yang and Tretinnikov; Nucl. Instrum. Meth. Phys. Res. B 151 (1999) 302-305], a mixture of photoinitiator and grafting reagent is applied to a polymeric substrate surface which is then exposed to sufficient UV light of the desired wavelength. This process requires the costs of an added ingredient (the photoinitiator) and an added step (application prior to UV irradiation). There is a need for a simpler, cheaper process.

An object of the present invention is to provide a process for modifying the surface of a polymeric material that does not adversely affect the bulk properties of the polymer.

Another object of the present invention is to provide a process that allows full surface coverage with a thickness of only about one molecular layer.

Another object of the present invention is to provide a process that permits penetration of a reagent into open structures in the polymeric material.

Another object of the present invention is to provide a process that is simple and cost-effective.

Another object of the present invention is to provide an efficient vapor-phase grafting process that does not use photoinitiators Another object of the present invention is to provide a one-step UV grafting process.

BRIEF SUMMARY OF THE INVENTION

The present invention is directed toward a process for modifying polymeric surfaces. In carrying out the process, a polymeric substrate is introduced into a processing chamber. The processing chamber is sealed and the oxygen content within the processing chamber is reduced. A flow of inert gas containing a grafting reagent may be provided. The polymeric substrate is then exposed to ultraviolet light at a wavelength below 200 nm, causing the polymeric substrate to undergo a free radical-induced surface change. Upon exposure to a grafting agent, the polymeric substrate forms chemical bonds with the grafting agent, resulting in a chemically modified polymer. The modification occurs primarily at the surface of the polymer, with little penetration beyond 100 nm, although the depth of penetration is dependent on the source and intensity of UV irradiation, as well as the structure and composition of the polymeric substrate. The resulting polymer may be advantageous relative to the original material in a number of ways.

The methods of the invention are suitable when used on many different polymer substrates, and are particularly useful with polyesters, particularly polyesters derived from terephthalic acid. The methods of the invention are applicable to polymeric substrates in any form, included molded articles, films, fibers, fabrics. In some preferred embodiments of the invention, the UV light is produced by a xenon excimer lamp (172 nm). When a xenon excimer lamp is applied to PET films, UV dose levels of between about 1 J/cm$^2$ and 32 J/cm$^2$ are typically employed. The methods of the invention can be applied in high-throughput production processes analogous to those used in the food packaging industry.

In some preferred embodiments, the grafting agent is introduced into the reaction chamber as a gas. In such embodiments, the grafting agent should have a sufficiently high vapor pressure to ensure that adequate quantities of the grafting agent are available for reaction. One can envision a nearly limitless collection of suitable grafting agents; some preferred grafting agents include fluoropolymers, silicones, hydrocarbons, and amines. The grafting agents must have chemical functionality that is amenable to reaction with free radical substrates. In the process described herein, the grafting agents become covalently bonded to the polymeric substrate, yielding a modified polymeric product in which the functionality provided by the grafting agents is permanently attached to the polymer, and is therefore non-fugitive.

DETAILED DESCRIPTION OF THE INVENTION

Figure 1:
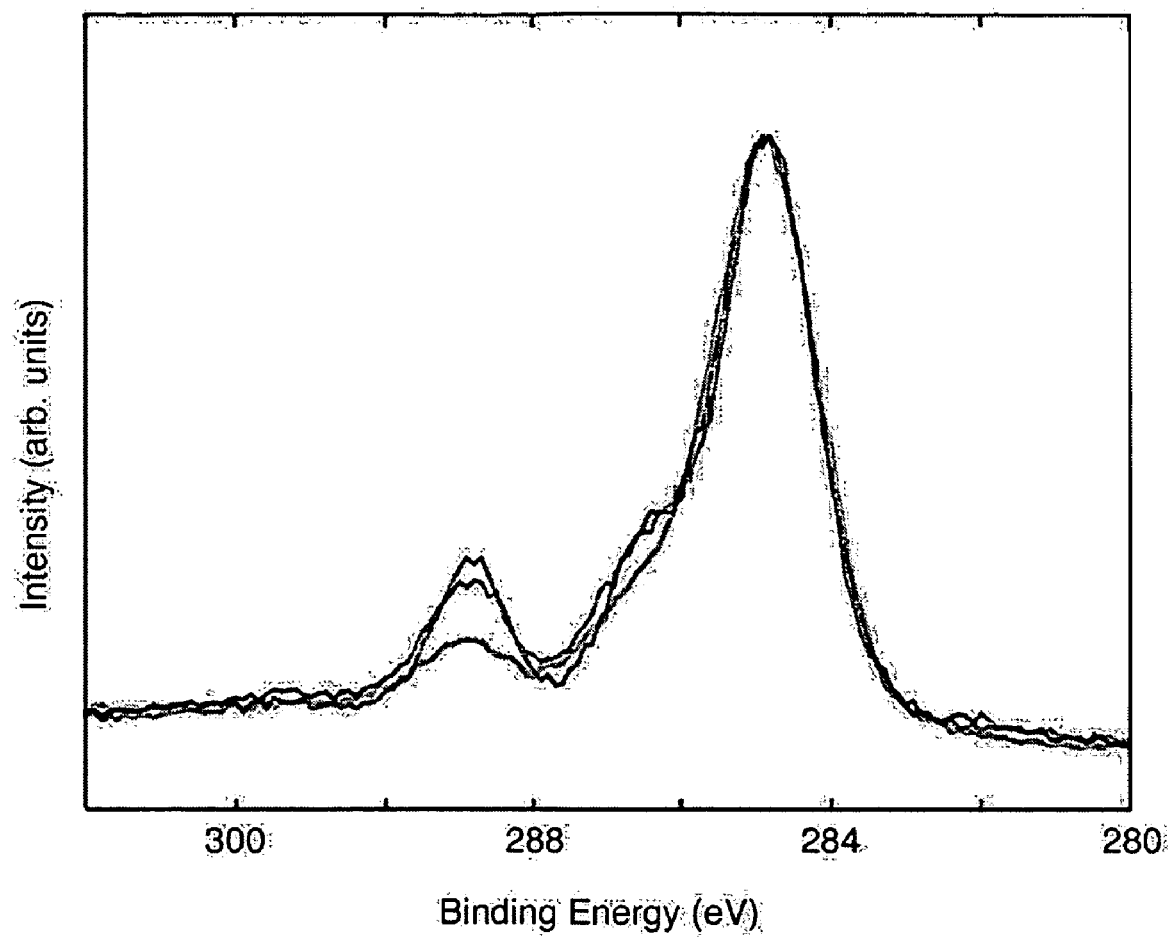
FIG. 1 provides a comparison of the C 1s region of: untreated PET film (upper curve at 288.5 eV), PET film irradiated at 248 nm (middle curve), and PET film irradiated at 193 nm (lowest curve).

As used herein, each of the following terms has the meaning associated with it as described below.

The articles "a" and "an" are used herein to refer to one or to more than one (i.e. to at least one) of the grammatical object of the article. By way of example, "an element" means one element or more than one element.

The term "organic chemical" refers to a chemical compound that contains carbon.

The term "excimer laser" refers to a laser wherein the lasing medium is a gas or gas mixture which is excited by an electrical discharge to form metastable molecular species that decompose with stimulated emission to yield light at substantially a single wavelength.

The term "excimer lamp" refers to a gaseous discharge lamp wherein the filling gas is excited by an electrical discharge to form metastable molecular species that decompose spontaneously with emission of light at substantially a single wavelength.

The term "grafting agent" refers to a chemical compound that can react with an irradiated PET substrate to form covalent chemical bonds with the polymeric substrate.

The polymeric substrate comprises any polymer known to those of ordinary skill in the art. Preferably, the polymer is a polyester polymer selected from the group consisting of: poly(ethylene terephthalate); poly(propylene terephthalate); and poly(butylene terephthalate). Most preferably, the polymeric substrate is poly(ethylene terephthalate).

When the polymeric substrate is polyester, the polyester polymer can be any thermoplastic polyester polymer, particularly a partially aromatic polyester, especially a polyester mainly derived from an aromatic diacid and an aliphatic diol. The preferred polyester polymer is polyethylene terephthalate. As used herein, polyethylene terephthalate means a polymer having ethylene terephthalate units in an amount of at least 60 mole % based on the total moles of units in the polymer. Preferably, the polymer contains ethylene terephthalate units in an amount of at least 85 mole %, more preferably at least 90 mole %, and most preferably at least 92 mole %, as measured by the mole % of ingredients added to the reaction mixture. Thus, a polyethylene terephthalate polymer may comprise a copolyester of ethylene terephthalate units and other units derived from an alkylene glycol or aryl glycol with a aliphatic or aryl dicarboxylic acid.

Polyethylene terephthalate can be manufactured by reacting a diacid or diester component comprising at least 60 mole % terephthalic acid or $C_1$-$C_4$ dialkylterephthalate, preferably at least 70 mole %, more preferably at least 85 mole %, even more preferably, at least 90 mole %, and for many applications will be at least 95 mole %, and a diol component comprising at least 60 mole % ethylene glycol, preferably at least 70 mole %, more preferably at least 85 mole %, even more preferably at least 90 mole %, and for many applications, will be at least 95 mole %. It is also preferable that the diacid component is terephthalic acid and the diol component is ethylene glycol. The mole percentage for all of the diacid component totals 100 mole %, and the mole percentage for all of the diol component totals 100 mole %.

In addition to units derived from terephthalic acid, the acid component of the present polyester may be modified with units derived from one or more additional dicarboxylic acids. Such additional dicarboxylic acids include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Examples of dicarboxylic acid units useful for modifying the acid component are units from phthalic acid, isophthalic acid, naphthalene-2,6-dicarboxylic acid, cyclohexanedicarboxylic acid, cyclohexanediacetic acid, diphenyl4,4'-dicarboxylic acid, succinic acid, glutaric acid, adipic acid, azelaic acid, sebacic acid, and the like, with isophthalic acid, naphthalene-2,6-dicarboxylic acid, and cyclohexanedicarboxylic acid being most preferable. It should be understood that use of the corresponding acid anhydrides, esters, and acid chlorides of these acids is included in the term "dicarboxylic acid".

In addition to units derived from ethylene glycol, the diol component of the present polyester may be modified with units from additional diols including cycloaliphatic diols preferably having 6 to 20 carbon atoms and aliphatic diols preferably having 3 to 20 carbon atoms. Examples of such diols include diethylene glycol, triethylene glycol, 1,4-cyclohexanedimethanol, propane-1,3-diol, butane-1,4-diol, pentane-1,5-diol, hexane-1,6-diol, 3-methylpentanediol-(2,4), 2-methylpentanediol-(1,4), 2,2,4-trimethylpentane-diol-(1,3), 2,5-ethylhexanediol-(1,3), 2,2-diethyl propane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, and 2,2-bis-(4-hydroxypropoxyphenyl)-propane.

Typically, polyesters such as polyethylene terephthalate polymer are made by reacting a glycol with a dicarboxylic acid as the free acid or its dimethyl ester to produce a prepolymer compound which is then polycondensed to produce the polyester. Polyesters can be prepared by conventional polymerization procedures well-known in the art sufficient to effect esterification and polycondensation.

Other components can be added to the composition of the present invention to enhance the performance properties of the polyester polymer. For example, crystallization aids, impact modifiers, surface lubricants, denesting agents, stabilizers, antioxidants, ultraviolet light absorbing agents, metal deactivators, colorants, nucleating agents, acetaldehyde reducing compounds, other reheat rate enhancing aids such as elemental antimony or reduced antimony, carbon black, graphite, black iron oxide, red iron oxide and the like, sticky bottle additives such as talc, and fillers and the like can be included. The resin may also contain small amounts of branching agents such as trifunctional or tetrafunctional comonomers such as trimellitic anhydride, trimethylol propane, pyromellitic dianhydride, pentaerythritol, and other polyester forming polyacids or polyols generally known in the art. All of these additives and many others and their use are well known in the art and do not require extensive discussion. Any of these compounds can be used in the present composition.

In carrying out the methods of the invention, the polymeric substrate is inserted into a processing chamber, which is substantially sealed and the oxygen content is reduced within the processing chamber. Typically, an inert gas is used to reduce the oxygen content. Preferably, the oxygen content is reduced by introducing nitrogen into the processing chamber. The processing chamber is equipped with a source of UV. Preferably, the source of UV light is an excimer lamp filled with xenon. A dielectric barrier discharge (DBD) excimer lamp has been used effectively as the UV radiation source. It will be appreciated that other types and configurations of excimer lamp may be employed to similar effect. The annular configuration of same consists of an inner quartz tube to carry cooling water, an annular space for the active gas, and a 43 mm diameter outer Suprasil® quartz tube, 50 cm in length. The lamp is operated at atmospheric pressure filled with undiluted Xenon gas (Spectra Gas Laser Grade) to produce 172 nm UV. The lamp is enclosed within a coaxial polycarbonate cylinder, sealed at the ends and continuously swept by boil-off from liquid nitrogen, thereby causing depletion of oxygen in the region. The polymer to be treated is attached to the inner surface of the cylinder, providing a constant distance to the lamp of about 7 cm. The irradiance at the sample position can be measured with an International Light Model 1400A photometer with a SED-185 detector head. The spectral energy distribution of the lamp and the detector response curve may not overlap perfectly, necessitating a correction factor to the meter reading to obtain the UV dose (a correction factor of 2 was used for reduction to practice). Average irradiance received at sample position is about 50 mW/cm$^2$. Multiple samples can be acquired at varying UV dose levels (dose levels of 4/cm$^2$, 8 J/cm$^2$, 16 J/cm$^2$, and 32 J/cm$^2$ for reduction to practice).

Once the polymeric substrate is inserted into the processing chamber, it is exposed to ultraviolet light having a wavelength below 200 nm. When suitable irradiation conditions are utilized, this causes the polymeric substrate to undergo a surface change. There is an optimum range of the amount of UV light to be delivered. Too little or too much is undesirable. Too little will not accomplish the treatment and too much will harm the polymer. The amount of UV light delivered is the product of the rate of delivery (UV lamp power) and the duration of delivery (treatment time); lamp power can be traded off against treatment time in any set of circumstances. Optimal results on PET were found when the polymeric substrate was exposed to about 172 nm UV light at a dose level less than about 16 J/cm$^2$. The effect of 172 nm irradiation on polymers in the absence of oxygen not substantially exceeding about 16 J/cm$^2$ is dominated by carbonyl elimination and acid group formation, in contrast with the effect of irradiation at other deep UV wavelengths seen in previous studies. This is an unexpected result for this particular wavelength of UV radiation. At UV dose levels substantially higher than about 16 J/cm$^2$, differential etching roughens semi-crystalline PET surface.

The pH level of the polymer surface due to such UV exposure is proportional to both the intensity of the impinging UV radiation, as well as the time of exposure. Therefore it is possible to control the surface acid concentration by controlling one or both of these variables. After the surface change occurs, the polymeric substrate is removed from the processing chamber.

In some embodiments, an inert gas is bubbled through a liquid comprising a grafting agent to generate a vaporized grafting agent. The vaporized grafting agent is introduced into the chamber wherein the grafting agent attaches to the surface of the polymeric substrate. Once the chamber has been purged with an inert gas, such as nitrogen, the vaporized or condensed form of the grafting agent is introduced into the chamber. Typical grafting agents have a vapor pressure at room temperature sufficient to volatilize and allow reaction at the requisite reaction temperature. A vapor pressure that is too low will result in insufficient grafting agent at the workpiece surface. In this case, the radicals generated by the UV light will simply form acid sites, as occurs in the absence of the agent. The substrate is exposed to the UV light for a time sufficient to deliver the required exposure, as indicated by the detector. After introduction of the grafting agent, the chamber is purged with inert gas to remove any residual grafting agent. The grafting agent may be recovered for future use. Typical grafting agents include amines, fluorocarbons, silicones and hydrocarbons.

When a grafting agent is applied to the polymeric substrate, various surface properties are imparted. When the polymeric substrate is a fabric, these properties include anti-microbial activity, soil repellency/release, water repellency and softness/suppleness. Additional properties include anti-soil, anti-slip, anti-wetting, and anti-microbial.

EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein. Methods and equipment used in the examples is described below.

Materials

Experiments were performed on polyester films of the following type: 12 μm thick commercial production Mylar® LB 48 film (available from Dupont). Materials used as vapor phase grafting reagents were n-nonane (99%, purchased from Aldrich), 1-octene (98%, Aldrich), 3,3,4,4,5,5,6,6,7,7,8,8,9,9,10,10,10-heptadecafluoro-1-decene (99%, Aldrich, hereafter "HFD"), N,N,N',N'-Tetramethyl-1,4-butanediamine (hereafter TMBADA, from Aldrich) and N,N,N',N'-Tetramethyl-2-butene-1,4-diamine (TMBEDA, from Aldrich).

Excimer Laser Exposures

A Lambda LPX 325i excimer laser having either an ArF (193 nm) or KrF (248 nm) fill was used, with the beam spread by a cylindrical lens to obtain the desired fluence as a single shot. Strips of the film having a width of 1 cm were rinsed with HPLC grade isopropanol and end-mounted in 35 mm slide holders. The irradiations were accomplished in a home-made chamber continuously swept by boil off from liquid nitrogen.

Excimer Lamp Exposures

Excimer lamp UV irradiations were accomplished with a dielectric barrier discharge (DBD) excimer lamp of our own construction. The annular configuration comprises an inner quartz tube to carry cooling water, an annular space for the active gas, and a 43 mm diameter outer Suprasil® quartz tube, 50 cm in length. The lamp was operated at atmospheric pressure filled with undiluted Xenon gas (Spectra Gas Laser Grade) to produce 172 nm UV. The lamp is enclosed within a coaxial polycarbonate cylinder, sealed at the ends, and continuously swept by boil-off from liquid nitrogen.

The following procedure was used in Examples 1-5 below. The material to be treated was attached to the inner surface of the enclosure, providing a constant distance to the lamp of about 7 cm. The irradiance at the sample position was measured with an International Light Model 1400A photometer with a SED-185 detector head. The spectral energy distribution of the lamp and the detector response curve do not overlap perfectly, necessitating a correction factor of 2 to the meter reading to obtain the UV dose. Average irradiance received at sample position is about 50 mW/cm$^2$. Multiple samples were acquired at UV dose levels of 4 J/cm$^2$, 8 J/cm$^2$, 16 J/cm$^2$, and 32 J/cm$^2$. In each case, a piece of polyethylene (PE) film was treated along with the PET. If subsequent XPS showed other than trace oxygen pick-up by the PE, the run was discarded. Grafting agents were introduced into the lamp enclosure by bubbling dry nitrogen through corresponding liquid at room temperature at a flow rate of about 10 SCFH. An additional nitrogen line was used to sweep the detector head to prevent contamination from the grafting chemicals.

Surface Analysis

Samples for surface analysis were rinsed with isopropanol (Fisher, HPLC grade) and then deionized water (>18M Ω) prior to introduction, with the exception of one set of samples exposed to 32 J/cm$^2$. XPS analysis of the 172 nm treated material was carried out with a Specs "PHOIBOS" system, using a Mg anode (1253.6 eV) operated at 15 kV and 200 W. To better reveal the surface functional group population, a complete set of samples was derivatized with silver trifluoroacetate by overnight (18 h) exposure to a 10$^{-2}$ M solution of AgOCOCF$_3$ in acetone and then washed repeatedly with acetone. XPS of the laser-irradiated materials employed a VG ESCALab, also with a Mg anode.

Time of flight secondary ion mass spectrometry (ToF/SIMS) provides a more sensitive surface analysis and is especially effective for polymers. We used a PHI "TRIFT II CE" instrument to raster a 200 μm×200 μm surface area with 15 keV gallium ion beam at 600 pA current with extraction voltage set at 7200 V. Data acquisition time was set for 5 min and sample surface received an ion dose of 2.4 E+11 ion/cm$^2$. Surface topography was characterized by atomic force microscopy (AFM) using a Digital Instruments "NanoScope® IV" scanning probe microscope in intermittent contact ("tapping") mode. The scan rate was set at 0.5 Hz to scan over multiple 2 μm×2 μm sampling areas. Second order flattening was applied to the data before surface roughness analysis.

Topographical analysis was carried out with AFM comparing treated and control materials in the following Examples. The Root-Mean-Square (RMS) surface roughness for all measured samples was between 1 nm to 2 nm, indicating no islands were formed by accumulation of hydrocarbon on PET surface and no excess surface disintegration results from UV expose under the maximum employed dose. The contact angle of distilled water at the surface of the film was measured with a Tantec CAM-MICRO Gonionmeter (error=±2°).

Microbiological Studies

Microbial response studies were carried out by the Food Microbiology Laboratory in the department of Animal and Food Sciences at University of Delaware.

*Escherichia coli* TV1058 were the target microorganisms for the preliminary effectiveness tests of antimicrobial films. *E. coli* TV1058 is a recombinant strain containing lac-promoter driven lux genes obtained from Van Dyk (DuPont Experimental Station, Wilmington, Del.). Cultures were stored in 30% (v/v) glycerol (Mallinckrodt, Paris, Ky.) and frozen at −40° C. until use. Cells were revived by inoculation into Tryptic Soy Broth (TSB, Difco, Detroit, Mich.) and incubation overnight for approximately 17 h at 37° C.

The following standard protocol was utilized. Overnight growth of bacteria was pelleted by centrifugation for 15 min at 2,700 g with an IEC Centra4B Centrifuge (International Equipment Company, Needham Heights, Mass.). The TSB supernatant was discarded and the pellet resuspended in 0.1% (w/v) Bacto-peptone (Difco) water. Centrifugation was repeated. The supernatant was discarded and the pellet was resuspended in 0.1% (w/v) Bacto-peptone (Difco). The same liquid medium was used for washing the cells, performing dilutions, and exposing the cells to the test film in solution. Bacto-peptone (0.1%, w/v, Difco) water was inoculated with the test culture to obtain a total volume of 25 mL in a 125-mL culture flask. Untreated and treated PET films were cut immediately prior to each experiment into pieces of approximately 2.5 $cm^2$ each with a total surface area of 350 $cm^2$. Untreated and treated films were added to two different flasks containing the cell suspensions. The flasks were agitated at 100 rpm on a Gyratory Shaker Model G2 (New Brunswick Scientific Co., Inc., New Brunswick, N.J.) during incubation. The liquid was sampled at 0, 1.5, 3 and 6 h to determine viable cell counts. Samples were serially diluted in 0.1% (w/v) Bacto-peptone (Difco) water. The liquid sample was spread-plated in duplicate with Tryptic Soy Agar (TSA, Difco). Plates were incubated overnight at 37° C. and colonies were counted manually. All experiments were duplicated.

Example 1

In this example, a polyester film was irradiated but no grafting reagents were used. Films were irradiated using the xenon excimer lamp in accordance with the procedure described above. The resulting treated samples were compared with untreated films, as well as films treated via irradiation at higher wavelengths.

The interpretation of PET core level spectral lines is well-established. The average intensity ratio of C 1s and O 1s peaks from three untreated PET samples is 10.00/4.24, which is close to the nominal value of 10/4. FIG. 1 shows data from the C 1s region of the untreated and two laser-treated materials. All spectra were shifted (so that the aliphatic carbon peaks appears at 284.6 eV) and normalized. They were not smoothed. The difference between the untreated material and that irradiated at 248 nm is small. In contrast, it is evident that UW irradiation of intensity 12 $mJ/cm^2$ at 193 nm leads to significant loss of both oxygen-related carbon species.

Figure 2:
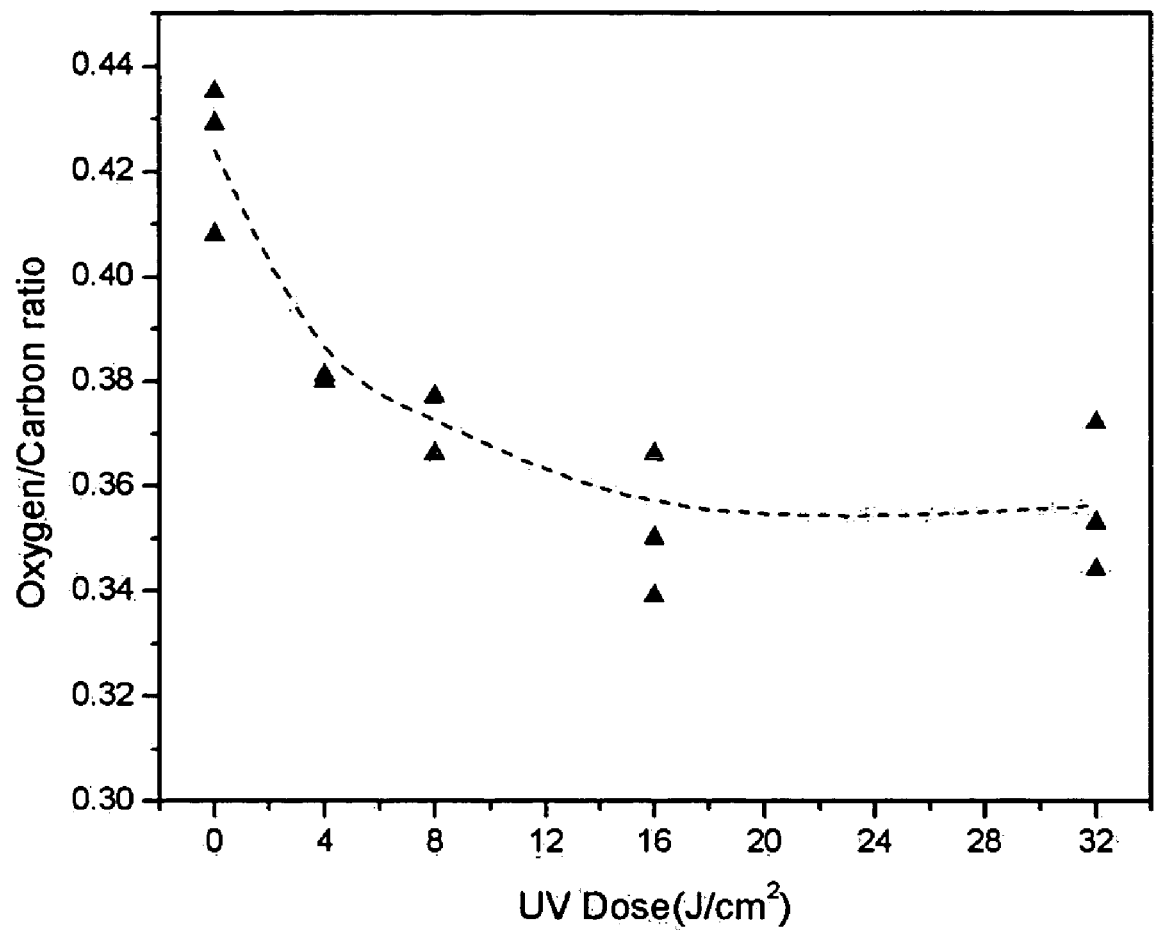
FIG. 2 shows the effect of 172 nm UV irradiation on surface oxygen content of PET as determined by XPS. The dashed line is only a guide for the eye.

The effect of 172 nm UV irradiation on the surface oxygen to total carbon ratio for three equivalent samples is depicted in FIG. 2. The ratio decreases with increasing UV dose up to about 16 $J/cm^2$, and then levels off at about one-sixth less than its original value. For films receiving 32 $J/cm^2$, the decrease of O/C ratio relative to that of untreated material was 8-10% greater for films analyzed as treated, compared to films rinsed before analysis. The unwashed film was also somewhat tacky to touch.

Figure 3:
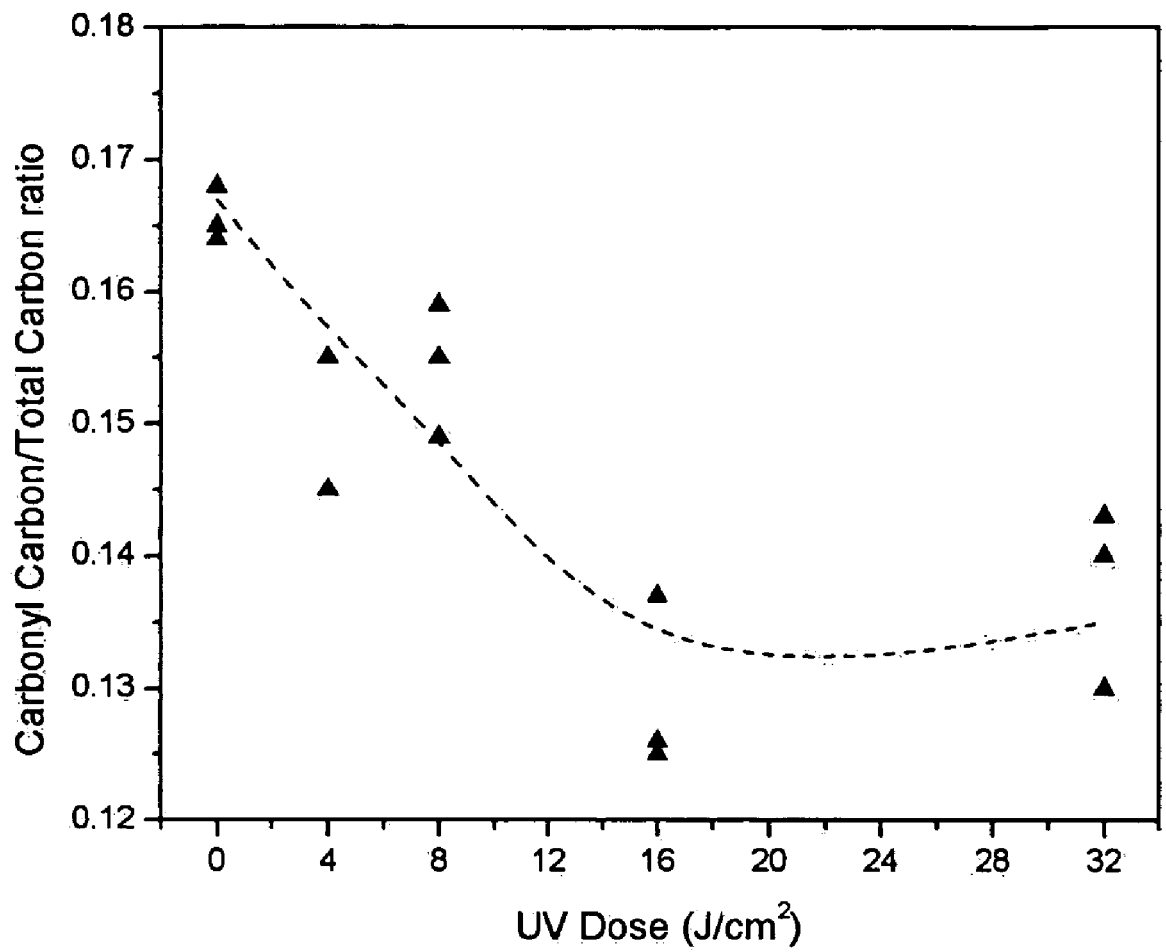
FIG. 3 shows the effect of 172 nm UV irradiation on the relative C=O content of surface carbon as determined by XPS. The dashed line is only a guide for the eye.
Figure 4:
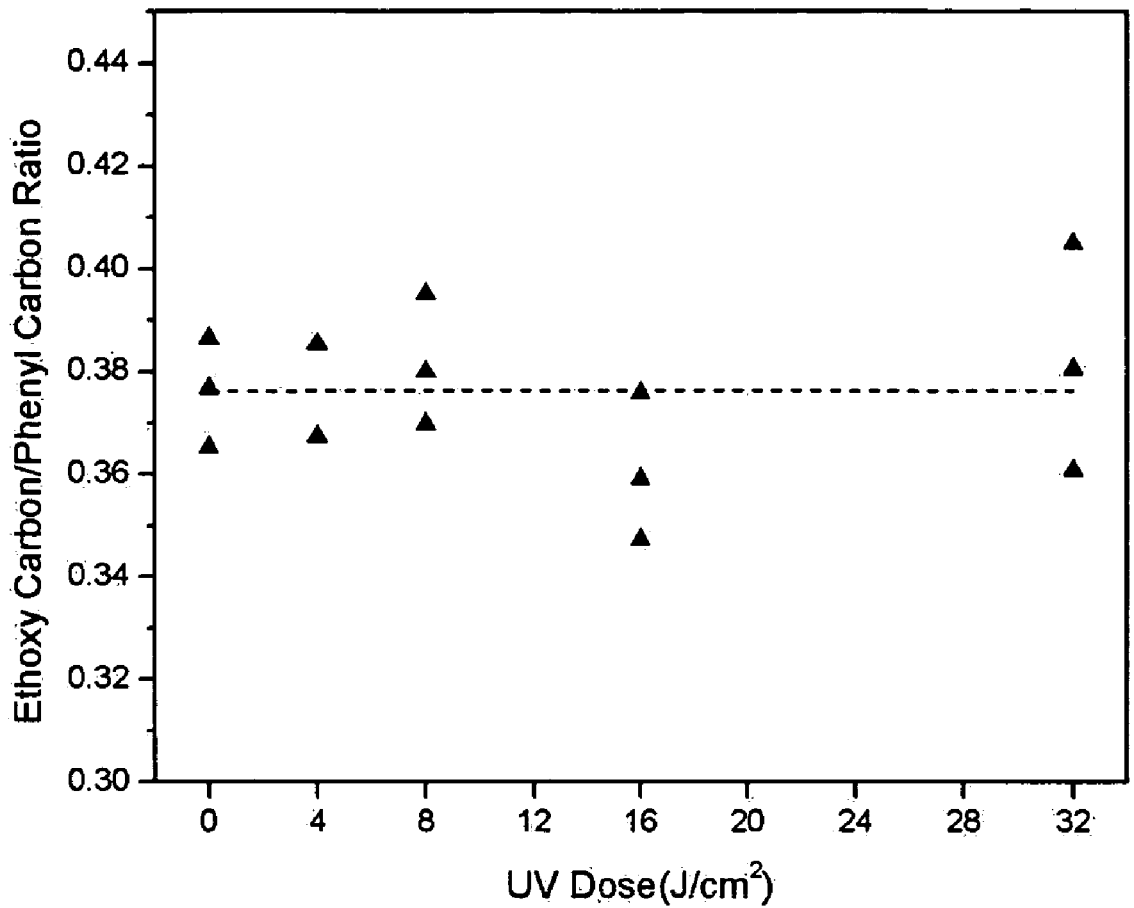
FIG. 4 shows the effect of 172 nm UV on $I_{C-O}/I_{C\ aromatic}$ as determined by XPS. The dashed line is only a guide for the eye.
Figure 5:
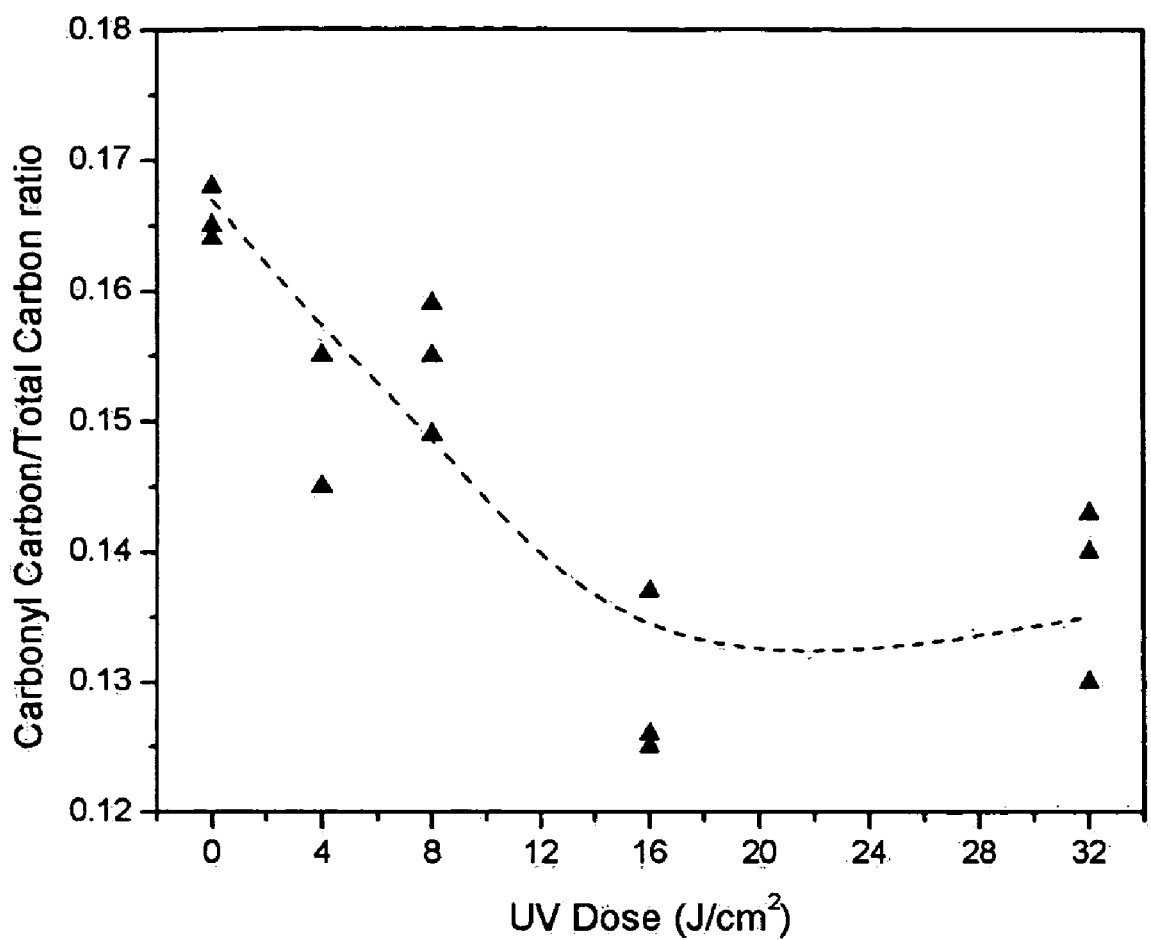
FIG. 5 shows the relationship between relative surface oxygen content and relative carbonyl content for PET treated by irradiation at 172 nm. The solid line is a model calculation assuming that oxygen content changes only via carbonyl content change.

Fitting the individual carbon peak components—carbonyl, ethoxy, and aliphatic—gives further insight. In untreated material, the measured average intensity ratio was 0.82/1.13/3.00, in reasonable agreement with the nominal value 1/1/3 and with previous studies of high purity PET. FIG. 3 shows that the loss of carbonyl carbon is similar to the decrease of total oxygen/carbon ratio, in contrast with the constancy of ethoxy carbon (FIG. 4). In fact oxygen loss closely tracks carbonyl carbon loss (FIG. 5).

Topographical analysis, carried out with AFM, was used to compare UV-treated and untreated PET samples. The Root-Mean-Square (RMS) surface roughness for samples that received 16 $J/cm^2$ or less was between 1 nm to 2 nm, but increased to above 4 nm for samples subjected to 32 $J/cm^2$. The observed cone structures in UV etched 32 $J/cm^2$ samples have diameters ranging from tens of nanometers to a few hundred nanometers, in good agreement with known dimensions of PET spherulites. This suggests that crystalline PET may be more resistant to degradation by deep UV light than amorphous material.

Figure 6:
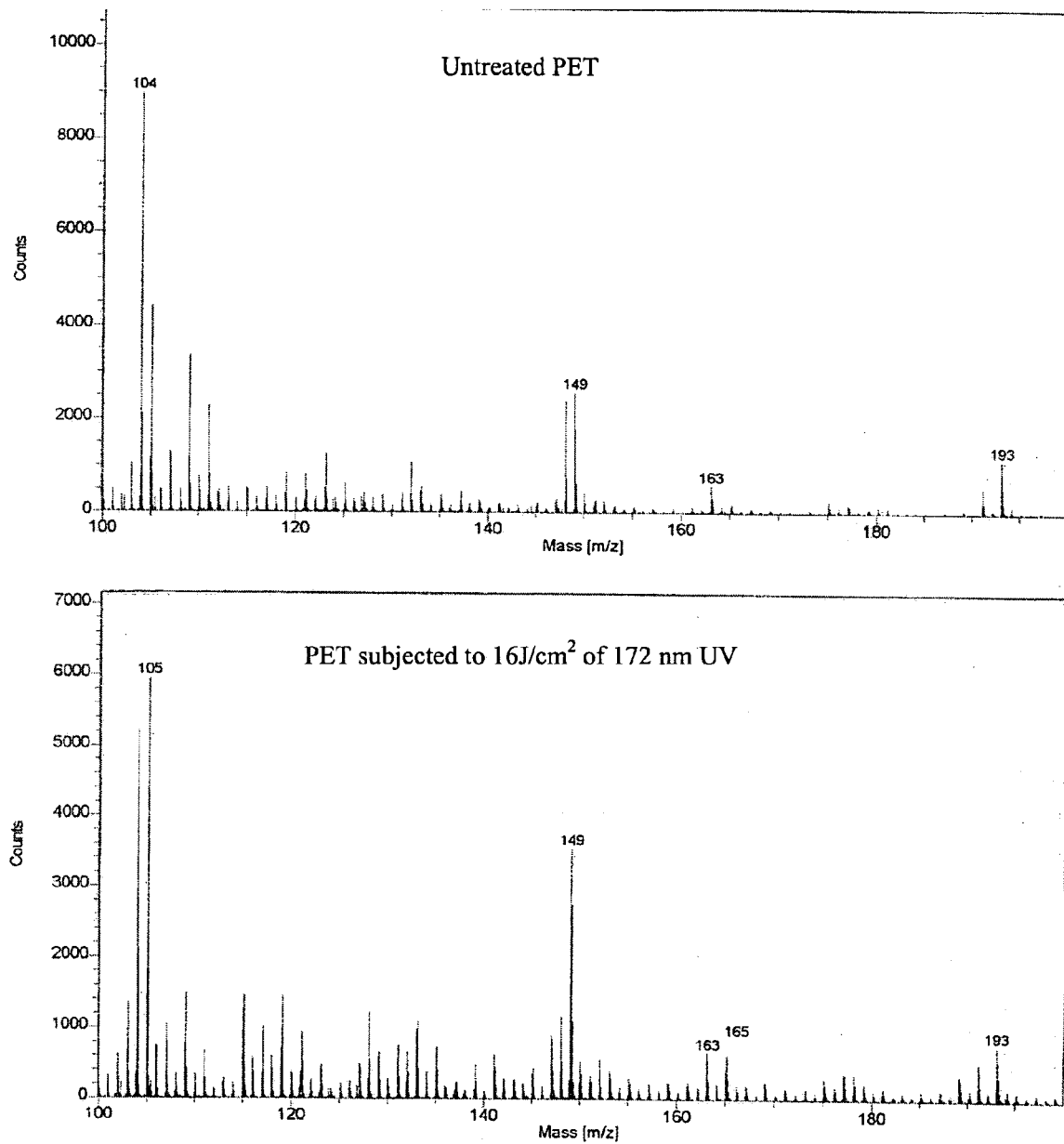
FIG. 6 shows TOF/SIMS positive ion spectra of untreated PET (top) and PET subjected to 16 J/cm$^2$ of 172 nm UV.

TOF/SIMS is a useful tool for studying polymer surface chemistry, and has been used in the past to study PET. As shown in FIG. 6, m/z=104, 105, 148, 149, 193 are characteristic peaks of PET. The mass peaks that appear in the UV-modified PET sample are similar to the original PET sample except for the differences in the relative intensities. In the UV-modified PET sample, the intensity ratios of high mass fragment m/z 149 (or m/z=105) to low mass fragment m/z 148 (or m/z 104) are much higher (2~3 fold) than the original PET. It may be attributed to preexisting polymer end groups that favor producing 149 m/z and 105 m/z peaks instead of their radical counterparts. In addition, peak intensity at m/z=165 also increases dramatically for the UV-treated material, perhaps originating from decarbonylation products.

In summary, the effect of 172 nm Xe excimer lamp irradiation on PET in the absence of oxygen up to 16 $J/cm^2$ is dominated by carbonyl elimination and acid group formation, in contrast with the effect of irradiation at other deep UV wavelengths seen here and in previous studies. At UV dose levels higher than 16 $J/cm^2$, differential etching roughens the semi-crystalline PET surface.

Example 2

In this example, 12 μm thick commercial production Mylar® LB 48 film (Dupont) was irradiated at 172 nm using the xenon excimer lamp. During irradiation, vapor phase grafting reagents (either n-nonane or 1-octene) were introduced into the reaction chamber by bubbling nitrogen through neat solutions of the grafting reagents.

Figure 7:
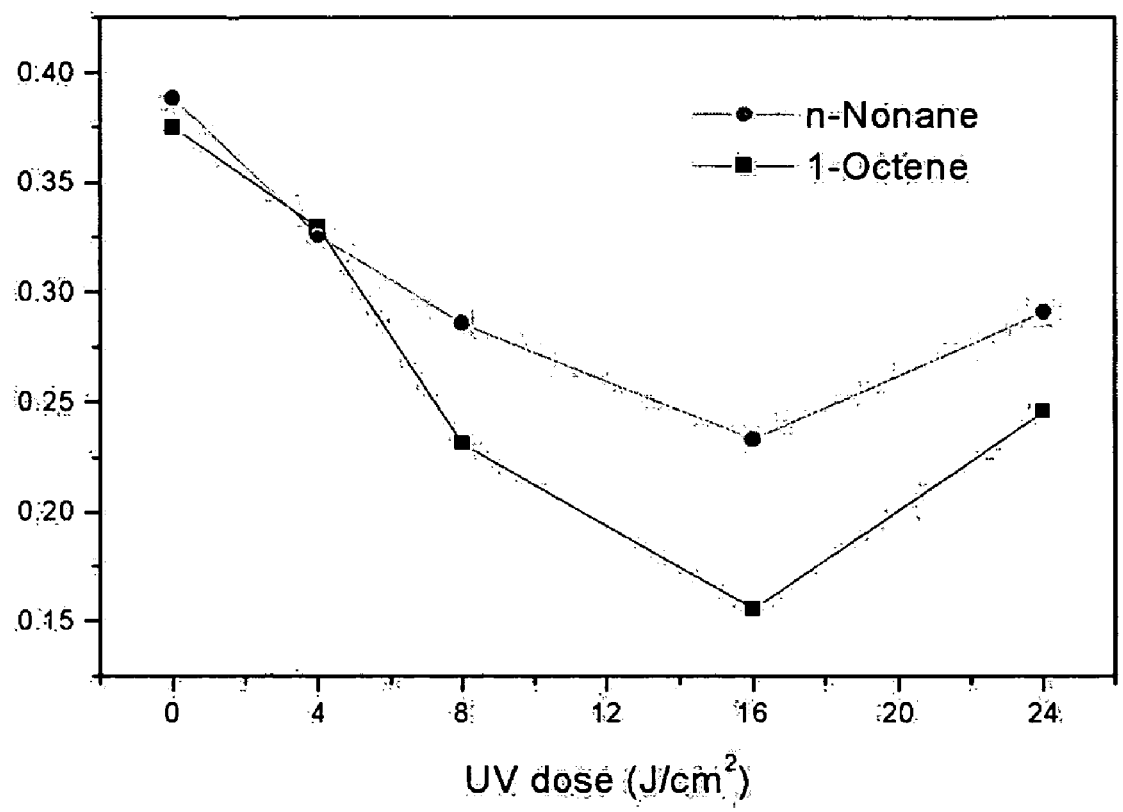
FIG. 7 shows the UV dose dependence of O/C ratio for both decene-grafted and nonane-grafted PET films.

XPS analyses show that both n-nonane and 1-octene were successfully grafted onto PET surfaces using 172 nm UV irradiation, as indicated by the lowered surface oxygen to total carbon ratio. FIG. 7 presents the UV dose dependence of O/C ratio for both nonane-grafted and 1-octene-grafted PET samples analyzed at 90° takeoff angles. The O/C ratio of the n-nonane-grafted sample decreased with increasing UV doses up to about 16 $J/cm^2$, and then returned to a higher O/C ratio upon further increases of UV dose. The increase of O/C ratio beyond 16 $J/cm^2$ is probably due to the disintegration of PET substrate at this dose level. The UV dose dependence of 1-octene-grafted samples was very similar to n-nonane-grafted sample, except that lower O/C ratios were reached at 16 $J/cm^2$ for the 1-octene-grafted samples, indicating that more 1-octene molecules were grafted onto PET surface under similar conditions.

Figure 8:
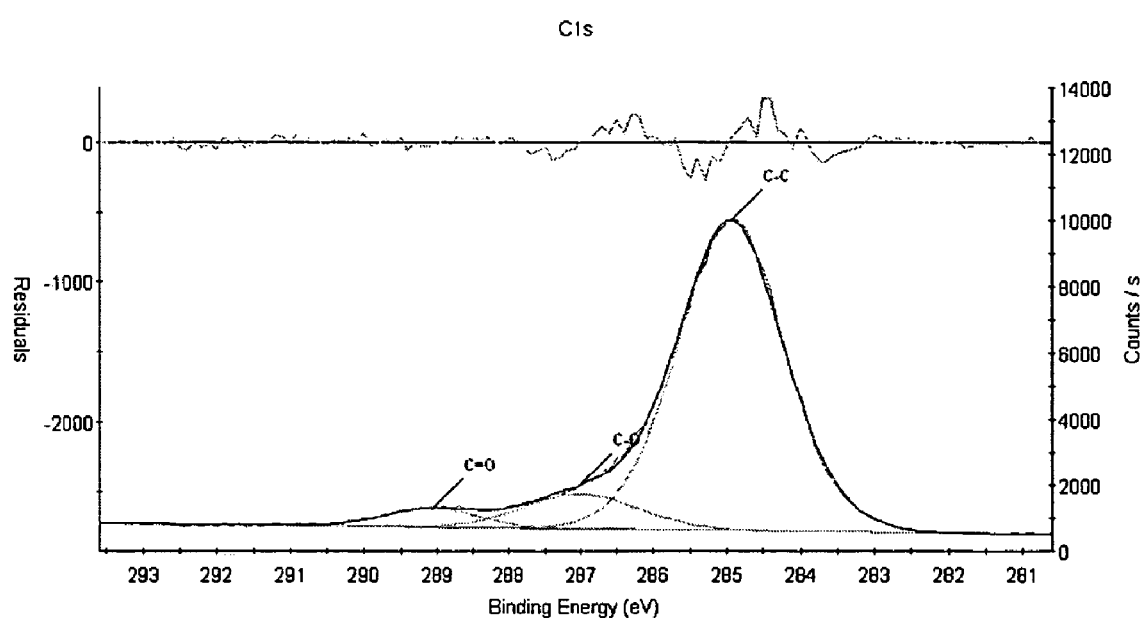
FIG. 8 shows the carbon 1s region of a typical 1-octene-grafted PET sample (16 J/cm$^2$ UV dose) at a 90° takeoff angle.

FIG. 8 shows the carbon 1s region of a typical 1-octene-grafted PET sample (16 $J/cm^2$ UV dose) at 90° takeoff angle. The spectra can be fit by three contributions, assigned to C═O, C—O, and C—C, from high binding energy to low binding energy, respectively.

O/C ratios were found in all cases to be further reduced when XPS analysis was performed at 30° takeoff angle. For example, a n-nonane-grafted PET sample (16 $J/cm^2$ UV dose) shows about 25% reduction in O/C ration, whereas a 1-octene-grafted PET sample (16 $J/cm^2$ UV dose) has a corresponding reduction of about 35%. Since the surface layer contributes more at the lower takeoff angle, this finding is consistent with the notion that grafted hydrocarbon exists as a thin distinct layer on the top of PET and that octene-grafted layers may be thicker than nonane grafted layers under similar processing conditions. The ToF/SIMS results below shed further light on this point.

Figure 9:
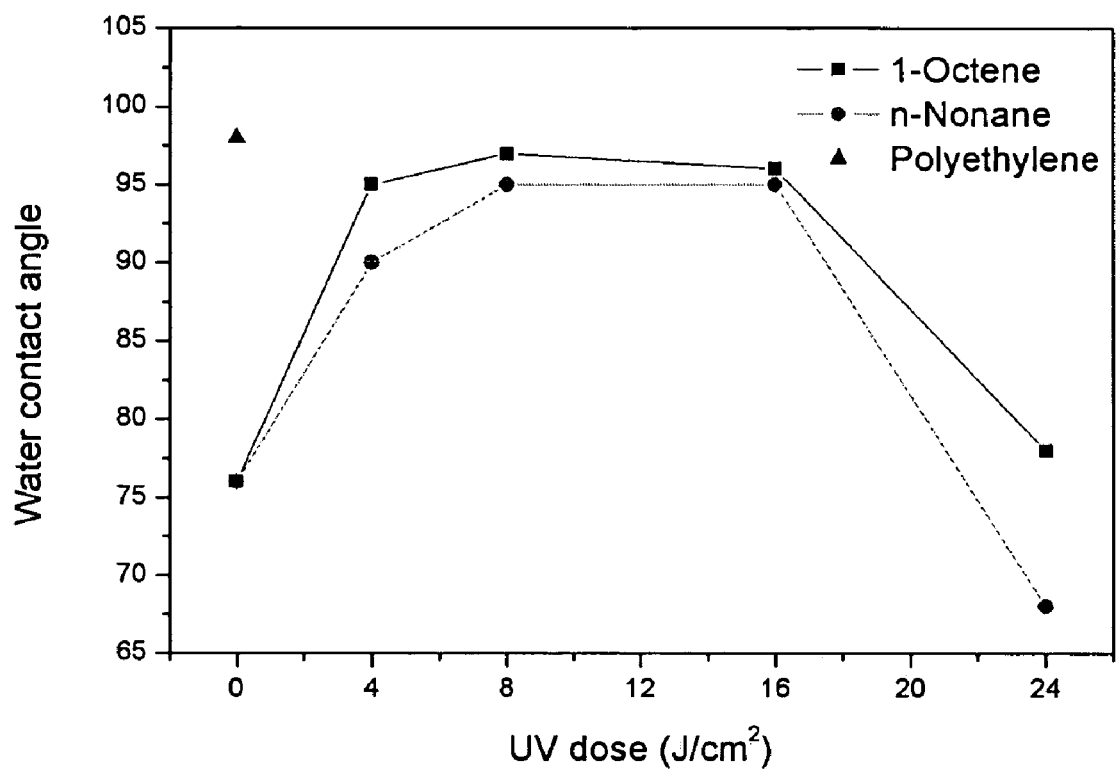
FIG. 9 shows water contact angle measurements of n-nonane-grafted PET and 1-octene-grafted PET as a function of UV dose level.

FIG. 9 presents water contact angle measurements of n-nonane-grafted and 1-octene-grafted samples at different UV dose levels. It is evident that increasingly hydrophobic surfaces have resulted from grafting up to a UV dose 16 J/cm$^2$, where the measured water contact angle approaches the measured value of pure polyethylene (98°). The water contact angle at higher UV dose decreases, consistent with the XPS results previously reported. However, water contact angle is only slightly affected by increase of the UV dose beyond 4 J/cm$^2$, while greater hydrocarbon uptake is suggested by XPS. This is consistent with the notion that the outermost surface material attains its final composition quite soon, while that of the near-surface region continues to evolve. In the absence of a grafting reagent (i.e., UV irradiation only), the water contact angle falls slightly to 70° over the same region and then remains constant with respect to UV dose.

TOF/SIMS provides detailed chemical structure information from the first and second layers of polymer surface. In the m/z=2~100 mass range, nonane-grafted and 1-octene-grafted material (16 J/cm$^2$ UV dosing) show fragment patterns characteristic of long chain hydrocarbons, m/z=15, 27, 29, 39, 41,43, 55, 57, 67, 69. In the mass range from m/z 100 to mn/z 200, nonane-grafted PET exhibits characteristic mass peaks of substrate PET, m/z=105, 149, 165, 193, whereas 1-octene-grafted PET shows no prominent mass peaks, consistent with long chain hydrocarbon spectra. There results suggest that 1-octene-grafted PET samples (16 J/cm$^2$ UV dose) are fully covered by hydrocarbon, but nonane-grafted PET samples may not be. As noted above, XPS shows some spectral features of PET for these materials. Their presence in the XPS and absence from the ToF/SIMS is consistent with the notion of a monomolecular graft layer on top of PET.

Topographical analysis was carried out with AFM comparing UV-grafted and untreated PET samples. The Root-Mean-Square (RMS) surface roughness for all measured samples is between 1 nm to 2 nm, indicating no islands are formed by accumulation of hydrocarbon on PET surface and no significant surface degradation results from UV exposure at intensities up to 16 J/cm$^2$ dose.

Example 3

Fluorocarbon HFD, containing an end carbon-carbon double bond, was investigated as a potentially useful grafting agent. In this example, 12 μm thick commercial production Mylar® LB 48 film (Dupont) was irradiated at 172 nm using the xenon excimer lamp. During irradiation, vapor phase HFD was introduced into the reaction chamber by bubbling nitrogen through a neat HFD solution.

Figure 10:
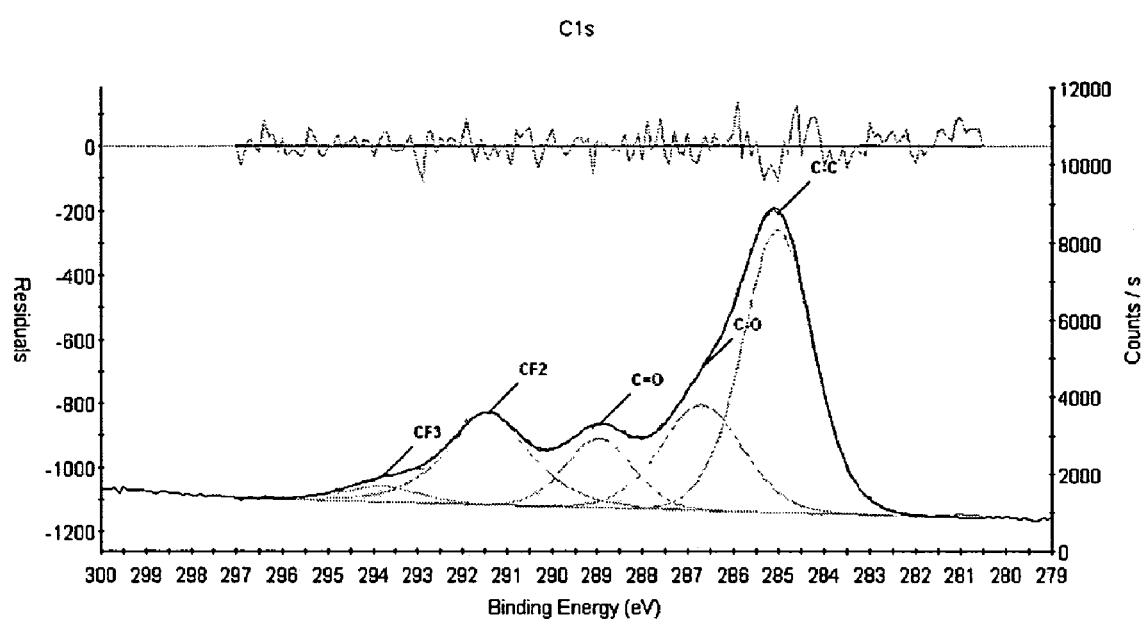
FIG. 10 shows the increase of near-surface fluorine content and decrease of water contact angle by grafting of fluorocarbon from heptadecafluoro-1-decene.
Figure 11:
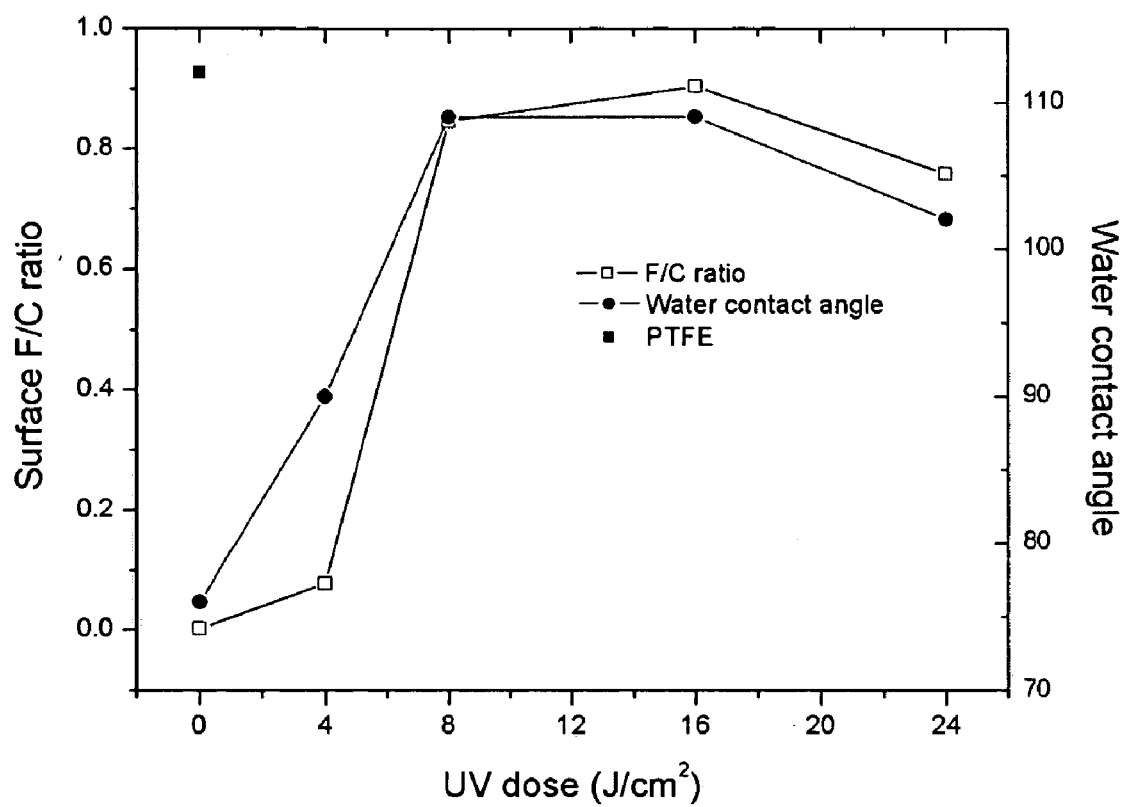
FIG. 11 shows XPS and water contact angle measurements of HFD-grafted PET samples as a function of UV dose (water contact angle of PTFE also shown).
Figure 12:
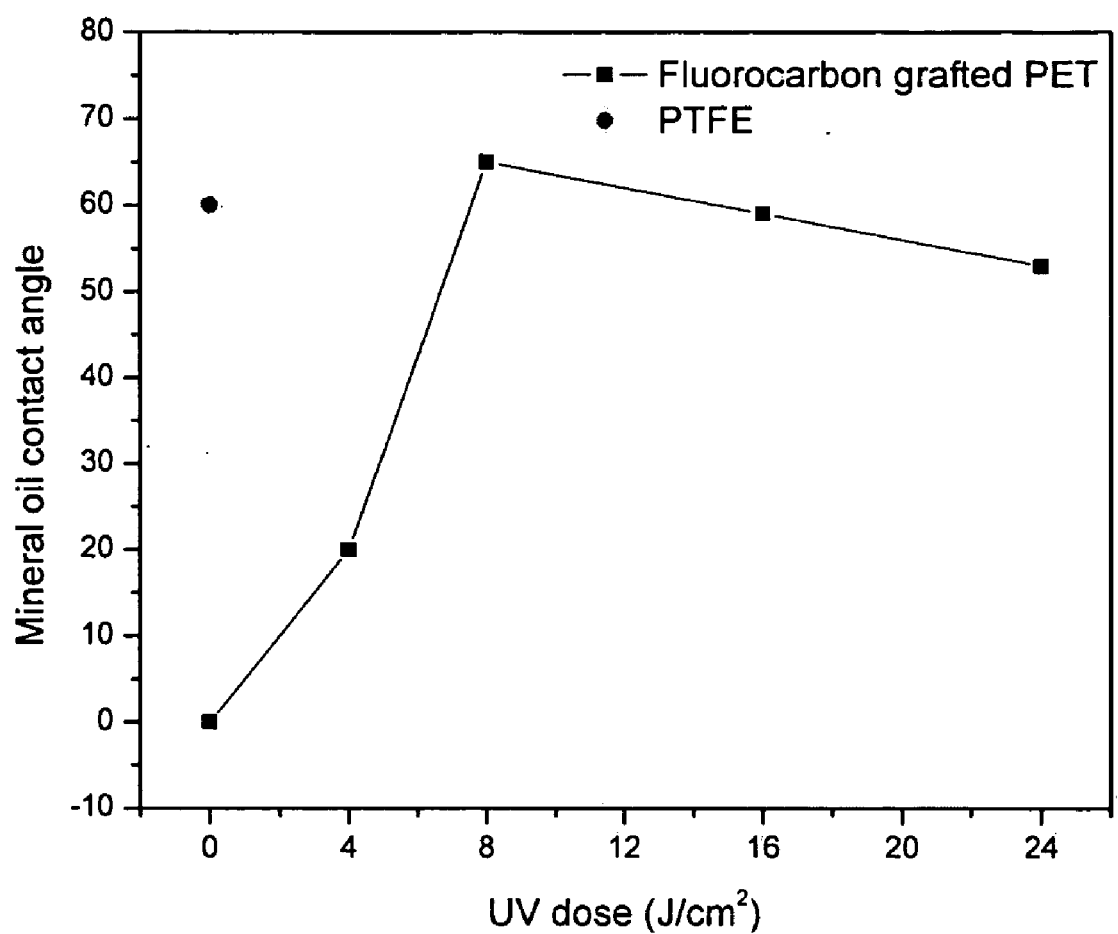
FIG. 12 shows mineral oil contact angle measurements of HFD-grafted PET samples at different UV doses (oil contact angle of PTFE also shown).

In general, fluorocarbons have very low surface energies, and thus are appealing as anti-soil coatings. FIG. 10 shows the carbon Is region at 90° takeoff angle from HFD-grafted PET (16 J/cm$^2$). The spectrum can be fit by five contributions, assigned to $CF_3$, $CF_2$, C=O, C—O, and C—C, from high binding energy to low binding energy, respectively. Both $CF_3$ and $CF_2$ originate from the grafted layer while the oxygen-containing species are derived from the substrate. FIG. 11 depicts the quantitative results of XPS and water contact angle measurements of HFD-grafted PET samples as a function of UV dose. As with the hydrocarbon-grafted PET, surface fluorine/carbon ratio from the XPS data collected at 90° takeoff angle increases with UV dose up to 16 J/cm$^2$ and then decreases at 24 J/cm$^2$. Water contact angle data also behaves similarly and reaches a maximum of 109°, approaching the water contact angle value of pure PTFE, 112°. The oil repellency of the HFD-grafted surface was characterized by mineral oil contact angle measurement (FIG. 12). The contact angle of mineral oil ranges from about 0° on untreated PET up to a maximum of about 65°, after HFD grafting at 8 J/cm$^2$ UV dose. Interestingly, this oil contact angle value exceeds that of pure PTFE, about 60°. The AFM measurements of HFD grafted samples show no signs of increased roughness, suggesting that the higher oil contact angle originates from a surface chemical difference between the pure PET and the grafted material.

ToF/SIMS data of HFD-grafted PET shows mostly characteristic mass fragments of typical fluorocarbons, with peaks observed at m/z=12, 31, 69, 119, 131, 169, 181, with some near noise level peaks (m/z=104, 105, 149) possibly originating from substrate PET.

XPS, ToF/SIMS, water and mineral oil contact angle measurements of HFD-grafted samples confirmed the presence of fluorocarbon on PET surfaces, providing the surfaces with oil and water repellency. Angle-resolved XPS was used to estimate the layer thickness (about 9 Å), consistent with the thickness of a self-assembled HFD monolayer. In addition, the higher oil contact angle observed on HFD-grafted surfaces than on PTFE surfaces supports the notion of self-assembled monolayers. Additional TOF/SIMS experiments with gold cluster ion gun revealed that some HFD molecules were connected to substrate PET from a linkage formed via phenylene radical addition to the C—C double bond in HFD.

Example 4

Antimicrobial activity can be imparted to PET surfaces by irradiating with 172 nm UV under $N_2$ purge and then derivatizing the photolytically modified surface with a silver salt. Silver trifluoroacetate reacts with PET surface carboxylic acid groups to yield surface-bound silver carboxylate salts according to the following reaction scheme:

R—COOH + $CF_3COOAg$ ⟶ R—COOAg + $CF_3COOH$

A commercially available polyester film (12 μm thick commercial Mylar® LB 48 PET film) was irradiated with a dielectric barrier discharge Xe excimer lamp of our own construction. The average irradiance received at the sample position was about 50 mW/cm$^2$. Multiple samples were acquired at UV dose levels of 4 J/cm$^2$, 8 J/cm$^2$, 16 J/cm$^2$, 24 J/cm$^2$ and 32 J/cm$^2$. Samples were first rinsed with acetone to remove soluble species from the surface, and then reacted overnight (18 h) with silver trifluoroacetate by exposing the UV-modified PET film to a 10$^{-2}$ M solution of $AgOCOCF_3$ in acetone. The derivatized samples were then rinsed with acetone and allowed to stand in pure acetone for 1 hour to allow unreacted silver to dissolve into solution.

Figure 13:
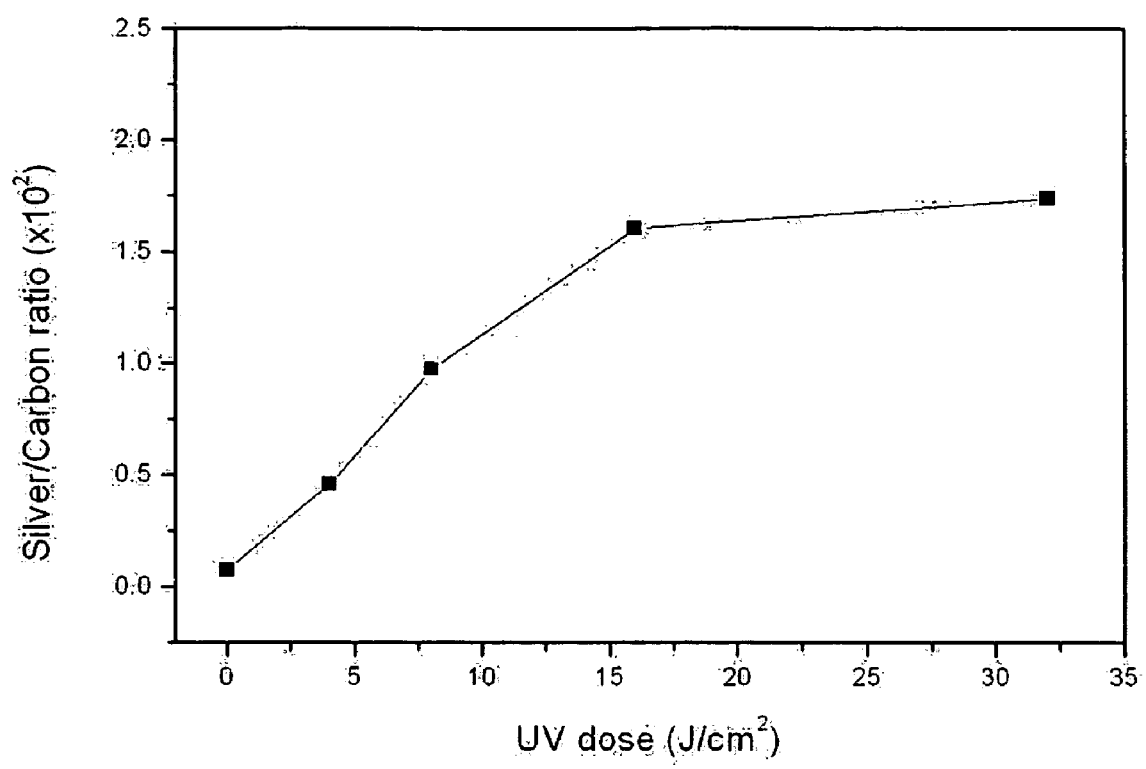
FIG. 13 shows the relative surface silver content of silver-derivatized PET as a function of UV dose administered to the PET film.

The Ag/C ratio increases with UV dose up to about 16 J/cm$^2$, as shown in FIG. 13, suggesting that formation of carboxylic acid end groups accompanies the other changes. Since the derivatization reaction proceeds only for surface-exposed acid groups, while the XPS signal originates from at least the top few nanometers, the Ag/C ratio likely understates the surface acid group concentration.

XPS spectra of the silver-derivatized 24 J/cm$^2$ 172 nm WV-treated PET at 90° takeoff angle indicated that C, O, and Ag were the major elements presented on the surface while residual silver trifluoroacetate were completely absent. A high resolution scan of the silver 3d core level emission determined that the majority of silver on the surface has a binding energy that is about 0.6 eV higher than metallic silver and is most likely surface-bound silver ions. A high resolution scan of fluorine 1s emission confirmed that the fluorine level on the derivatized surface was undetectable with XPS. When the takeoff angle of XPS analysis was reduced from 90° to 30°, reducing the sampling depth in half, the Ag/C ratios increased about 1.5-fold, suggesting that the silver ions were enriched on the outer surface, where they would be most available to microbes.

Preliminary antimicrobial activity assessment was carried out on samples exposed to 24 $J/cm^2$ UV by adding treated films into *E. Coli* TV 1058 culture with an initial population of $10^6$ cfu $mL^{-1}$ at 27° C., following the previously described protocol. A 6-$log_{10}$ reduction was observed with 6 hours of incubation, whereas no reduction was observed with untreated films. This indicates a strong antimicrobial activity of the treated film against *E. Coli* TV 1058.

Example 5

Various amine-containing species can be grafted to UV-modified polymer substrates to impart antimicrobial or other useful properties. In this example, two tertiary amine species, N,N,N',N'-Tetramethyl-1,4-butanediamine (TMBADA) and N,N,N',N'-Tetramethyl-2-butene-1,4-diamine (TMBEDA) were grafted, as gases, onto UV-modified polyester films. Additionally, other amines were grafted as liquids onto UV-modified polyester films. Aminoethylethanolamine (AEEA), JEFFAMINE® D-230 polyoxypropylenediamine (D-230), and JEFFAMINE T-403 polyoxypropylenetriamine (T-403) were applied as liquids to the PET surface and then subjected to 172 nm UV exposures under constant nitrogen purge.

The vapor-phase grafting agents were introduced into the lamp enclosure by bubbling dry nitrogen through corresponding liquid at room temperature at flow rate about 10 SCFH. An additional nitrogen line was used to sweep the detector head to prevent contamination from the grafting chemicals. Due to the absorptivity of the amines at the spectrum range of our xenon excimer lamp, the recorded UV exposure dose from the photometer is not an absolute value but only serves as a reference for samples exposed at different runs. These as-treated grafting samples were then subjected to bio-testing.

Further derivatizations were also carried out for some of the amine-grafted samples. Tertiary amine salts were acquired by exposure to hydrochloric acid (33%~38%, Fisher Scientific) vapor for 10 mins. Quaternary amines were acquired by stirring grafted samples in 1-bromopropane at 50° C. for 24 h. The residual 1-bromopropane was rinsed away with isopropanol.

XPS results of PET films grafted with vapor-phase amines are displayed in Table 1. The UV dose that is listed in Table 1 represents the photometer readout, not the actual dose received by the samples. The term "FWHM" refers to the full width of a peak at half of its maximum height.

TABLE 1

XPS results of amine grafted PET samples.

| Materials | UV dose $(J/cm^2)$ | Core level | FWHM (eV) | Center (eV) | Atomic ratios to carbon |
|---|---|---|---|---|---|
| TMBADA/PET | 8 | C1s | 2.45 | 284.6 | 1.000 |
|  |  | N1s | 2.86 | 399.7 | 0.109 |
|  |  | O1s | 3.11 | 531.8 | 0.196 |
| TMBADA/PET | 16 | C1s | 2.32 | 284.6 | 1.000 |
|  |  | N1s | 3.01 | 399.8 | 0.105 |
|  |  | O1s | 3.18 | 531.9 | 0.187 |
| TMBEDA/PET | 8 | C1s | 2.18 | 284.6 | 1.000 |
|  |  | N1s | 2.02 | 399.6 | 0.116 |
|  |  | O1s | 2.83 | 532.2 | 0.088 |
| Nylon-6,6 | 0 | C1s | 1.85 | 284.6 | 1.000 |
|  |  | N1s | 1.75 | 399.8 | 0.160 |
|  |  | O1s | 1.92 | 531.2 | 0.177 |

Figure 14:
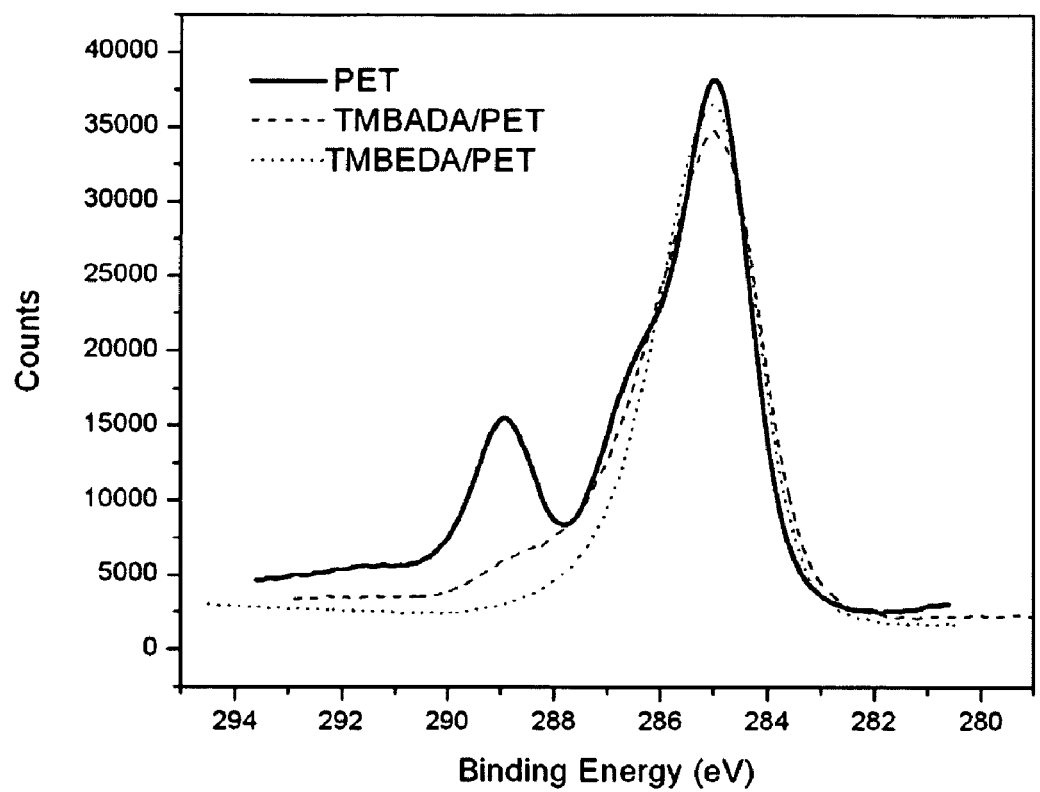
FIG. 14 compares C1s XPS peaks of TMBADA-grafted PET, TMBEDA-grafted PET, and untreated PET samples (spectra were shifted to set aliphatic C1s at 285 eV).

Based on the surface radical grafting mechanisms, both saturated (TMBADA) and unsaturated (TMBEDA) tertiary amines can be grafted onto PET surfaces. Table 1 show a high loading of nitrogen (8~10% atomic) on grafted surfaces (90° takeoff angle). When comparing grafting under different UV dose levels, we did not uncover any apparent benefits when samples were exposed to doses greater than 8 $J/cm^2$ UV under the current settings (although this should not be interpreted as precluding higher levels). We thus focused our preliminary experiments on samples obtained using dosages of 8 $J/cm^2$. Although similar in atomic composition, TMBADA-grafted samples have significantly wider N1s peaks (FWHM=~3 eV) than those of the TMBEDA-grafted samples (FWHM=~2eV). A nylon-6,6 sample standard (obtained from DuPont) analyzed under the same setting had a FWHM of 1.7~1.8 eV, suggesting that there are multiple nitrogen species with different chemical environments presented in TMBADA-grafted sample surfaces, whereas a single nitrogen chemical species might instead dominate the TMBEDA-grafted ones. FIG. 14 shows core level C1s emission peaks of both 4 $J/cm^2$ TMBADA-grafted and TMBEDA-grafted samples along with that of untreated PET. The small C1s peak at the high binding energy side (288.9 eV) is attributed to carbonyl carbon from PET substrate. It only appears as a very low intensity shoulder in TMBADA-grafted samples and was almost undetectable in TMBEDA-grafted samples, suggesting that the grafted layers were relatively thick. In addition, a shallower takeoff angle (30°) appears to have little effect on elemental ratios detected by XPS, suggesting that the surface layer is relatively uniform in depth within the XPS sampling range (~10 nm). Both tertiary amine compounds were readily grafted onto the PET substrate with only 8 $J/cm^2$ UV delivered to the substrate. Accordingly, we suspect that the photochemistry of grafting agents themselves may have played an important role in amine grafting applications.

Chemical derivatization of the surface reveals additional information about the chemical properties of the grafted layer. Since hydrochloric acid vapor should only react with free amine and be retained in the grafted layer (untreated PET shows no chlorine uptake), chlorine uptake is a good indication of the active amine level in the grafted materials. The chlorine uptakes of TMBEDA-grafted samples are about 4% of the atomic concentration, accounting for about 45% of the grafted amine. A new nitrogen peak also appears at a binding energy 2.3 eV higher than the original one, due to the formation of ammonium salts. Resolving this doublet confirmed that 45% of the nitrogen species were converted to ammonium salt. In contrast, the chlorine uptakes of the TMBADA-grafted samples were mostly less than 1%, accounting for about 15% of the grafted nitrogen species, and only slight enhancement of intensity at the high binding energy side of the peak was observed.

Similarly, a quaternization reaction of PET-grafted samples with 1-bromopropane may also help to reveal active amine content.

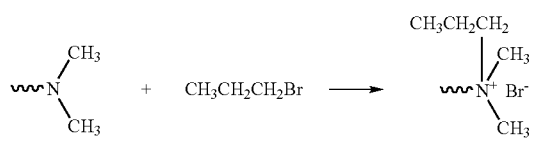

Figure 15:
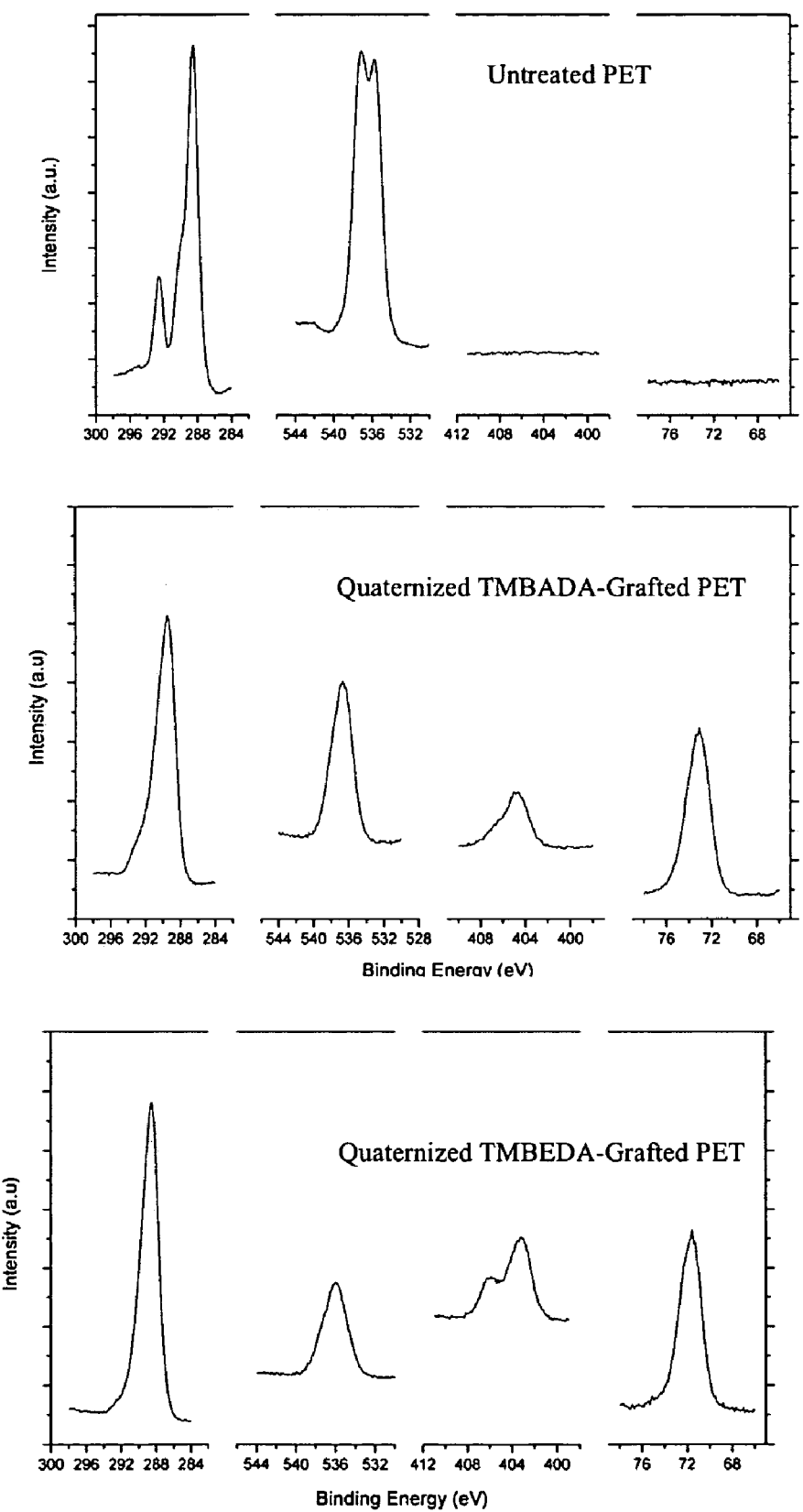
FIG. 15 shows XPS spectra of untreated PET film, quaternized TMBADA-grafted PET film, and quaternized TMBEDA-grafted PET film.

FIG. 15 shows XPS spectra of quaternized grafting samples and blank control samples. Bromide contents of the TMBEDA-grafted samples were again higher than those of the TMBADA-grafted samples. A new nitrogen peak resulting from the product quaternary amines appeared at a binding energy 2.4 eV higher than the N1s peak of the pre-quaternized TMBEDA graft-samples, whereas only slight enhancement was observed at the high binding energy side of N1s peak of the TMBADA graft-samples. Both chlorine derivatization and amine quaternization results indicate that higher amounts of active amine groups were preserved in the TMBEDA grafting process than in the TMBADA grafting process. However, in both cases, derivatization reactions occur throughout the grafted layer and thus are sensitive to layer thickness. In addition, some active amine species may not be accessible to derivatization due to the steric effect arising from non-bonded repulsions. Thus, the exact percentage of active surface-exposed amine species may be higher than the estimates derived from derivatization experiments.

Figure 16:
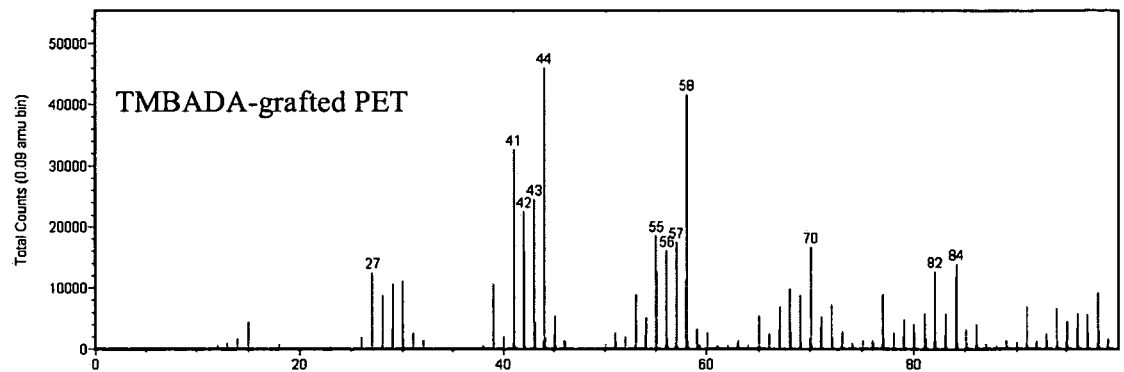
FIG. 16 shows TOF/SIMS spectra of TMBADA-grafted PET film and TMBEDA-grafted PET film.
Figure 16:
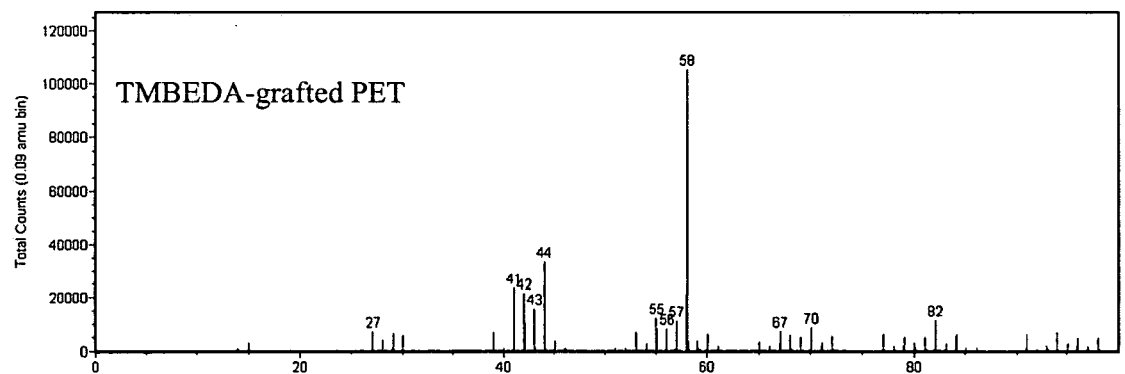

TOF/SIMS spectra of both TMBADA and TMBEDA-grafted samples in the 2~100 amu range are shown in FIG. 16. Peaks at m/z=58, a characteristic fragment of the tertiary amine group, are intense in both cases. The major difference between these two samples is the relative intensity of this mass fragment. The m/z 58 peak rises much higher than other peaks in TMBEDA-grafted samples whereas it is only a moderate intensity peak (second to m/z 44) in TMBADA-grafted samples.

The preliminary antimicrobial activity assessments were carried out by adding treated films into *E. Coli* TV 1058 cultures with an initial population of $10^6$ cfu $mL^{-1}$ at 27° C. In the case of TMBADA-grafted samples, a 0.3-$\log_{10}$ reduction was observed with 6 hours of incubation, suggesting only mild inhibition of bacterial growth. TMBEDA-grafted samples appeared to be more promising, as a 2.5-$\log_{10}$ reduction was observed with 24 hours of incubation (more than 99% bacteria were killed.).

PET grafting with liquid amines was also achieved. Table 2 lists the XPS analysis results of the grafted surfaces, demonstrating that liquid phase amines may also be grafted onto PET surfaces. The grafting processes appeared to be less efficient in the liquid phase than in the vapor phase. Grafting of solution phase agents is significantly disadvantageous relative to grafting of vapor phase agents, due to the decreased grafting efficiency and additional steps required to remove the solution phase grafting agents.

TABLE 2

XPS analysis of liquid amine grafted PET.

| UV dose | N/C ratio of the grafted surface | | |
|---|---|---|---|
| (J/cm$^2$) | AEEA | D-230 | T-403 |
| 0 | 0.004 | 0.003 | 0.00 |
| 4 | 0.019 | 0.038 | 0.009 |
| 8 | 0.039 | 0.073 | 0.014 |
| 16 | 0.043 | 0.073 | 0.078 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the representative embodiments of these concepts presented below.

The appended claims are intended to be construed to include all such embodiments and equivalent variations.

We claim:

1. A process for modifying polymeric surfaces, the process comprising the steps of:
    a) exposing the polymeric substrate to ultraviolet light having a wavelength below 180 nm wherein the polymeric substrate undergoes free radical-induced chemical changes; and
    b) reacting the polymeric substrate with a grafting agent such that covalent chemical bonds are formed between said grafting agent and said polymeric substrate in a one-step process under the influence of said ultraviolet light having a wavelength below 180 nm, resulting in a polymeric surface modified by the grafting agent;

wherein the polymeric substrate comprises a polyester, wherein said grafting agent is in the vapor phase, and wherein said grafting agent is a saturated hydrocarbon.

2. The process of claim 1, wherein the polymeric substrate is selected from the group consisting of: polymeric film and polymeric fabric.

3. The process of claim 1, wherein the polymeric substrate comprises a polyester selected from the group consisting of: poly(ethylene terephthalate); poly(propylene terephthalate); and poly(butylene terephthalate).

4. The process of claim 1, wherein said ultraviolet light is produced by an excimer lamp.

5. The process of claim 4, wherein said ultraviolet light is produced by a xenon excimer lamp.

* * * * *